United States Patent [19]
Varrichio et al.

[11] Patent Number: 5,186,170
[45] Date of Patent: Feb. 16, 1993

[54] SIMULTANEOUS RADIO FREQUENCY AND MAGNETIC FIELD MICROPROCESSOR RESET CIRCUIT

[75] Inventors: Anthony J. Varrichio, Flanders; William L. Winstrom, Andover, both of N.J.

[73] Assignee: Cyberonics, Inc., Webster, Tex.

[21] Appl. No.: 802,735

[22] Filed: Dec. 5, 1991

Related U.S. Application Data

[62] Division of Ser. No. 434,985, Nov. 13, 1989, Pat. No. 5,154,172.

[51] Int. Cl.⁵ ............................................. A61N 1/00
[52] U.S. Cl. ...................................................... 128/419 R
[58] Field of Search ................. 128/419 PG, 419 PT, 128/421, 422, 423 R

[56] References Cited

U.S. PATENT DOCUMENTS

| | | | |
|---|---|---|---|
| 3,182,246 | 5/1965 | Lloyd | 323/276 |
| 3,471,770 | 10/1969 | Haire | 328/173 |
| 3,649,906 | 2/1972 | Carpentier et al. | 323/274 |
| 4,066,086 | 1/1978 | Alferness et al. | 128/419 PG |
| 4,124,031 | 11/1978 | Mensink et al. | 128/419 PT |
| 4,202,342 | 5/1980 | Keller, Jr. | 128/419 PG |
| 4,203,447 | 5/1981 | Keller, Jr. et al. | 128/419 PG |
| 4,302,726 | 11/1981 | Shobbrock | 323/275 |
| 4,442,397 | 4/1984 | Ishikawa et al. | 323/275 |
| 4,592,360 | 6/1986 | Lesnick | 128/419 PS |
| 4,702,254 | 9/1989 | Zabara | 128/421 |
| 4,810,948 | 3/1989 | Takuma | 323/281 |
| 4,830,006 | 5/1989 | Haluska | 128/419 PG |
| 4,880,005 | 11/1989 | Pless et al. | 128/419 PG |
| 4,947,101 | 8/1990 | McVey | |
| 4,962,350 | 10/1990 | Fukuda | 323/285 |

OTHER PUBLICATIONS

Medtronic, Inc., "Minix 8240/8341/8342 Technical Manual", 1988, p. 41.
Schematic of Muscle Stimulator, date prior to Nov. 13, 1989.

*Primary Examiner*—William E. Kamm
*Attorney, Agent, or Firm*—Pravel, Gambrell, Hewitt, Kimball & Krieger

[57] ABSTRACT

An implant for stimulating the vagus nerve receives commands over a radio frequency link. The implant disables a voltage convertor used in providing the stimulation signal at periodic intervals to monitor for communications attempts. The implant provides radio frequency marker pulses before providing stimulation signals of certain frequencies. During the providing of stimulation signals the implant monitors the voltage overhead present between the voltage source and the load and adjusts the overhead to a desired level. The implant changes the voltage applied to certain internal components during stimulation periods to allow full power operation during those intervals and reduced power levels at other intervals. The implant is reset by the placing a magnet in a given location in conjunction with the application of a radio frequency transmission for a given period.

6 Claims, 9 Drawing Sheets

SIMULTANEOUS RADIO FREQUENCY AND MAGNETIC FIELD MICROPROCESSOR RESET CIRCUIT

This is a divisional of application Ser. No. 434,985, filed Nov. 13, 1989, now U.S. Pat. No. 5,154,172.

BACKGROUND OF THE INVENTION

1. Field of the Invention

The invention relates to implantable medical stimulators, and more particularly to stimulators which produce an electrical stimulation signal.

2. Description of the Related Art

Epilepsy and other similar motor disorders are associated with abnormal neural discharge patterns. Several different treatment techniques and methods involving applying an electrical signal to stop or reduce seizures were described in U.S. Pat. No. 4,702,254 to Dr. Jacob Zabara, which patent is hereby incorporated by reference in this specification. One technique involved determining when an epileptic seizure was about to occur and applying an electrical signal to the vagus nerve. The other technique suggested periodically applying a signal to the vagus nerve even if an aura or other condition was not sensed. Possible treatment periods were suggested. The patent further disclosed a high level block diagram of a circuit for applying electrical signals to the vagus nerve. The signals could be varied between stated limits. The limits were stated as being programmable by use of a reed switch whose openings and closings are controlled by an external programmer and electromagnet.

Conventional implantable medical stimulators such as pacemakers and drug infusion pumps are ordinarily based on custom integrated circuits which are quite complex, and therefore expensive, and use complicated pulse position communications techniques to transfer information between the implant and an external programmer The custom circuitry is developed because of the need to keep power consumption at a minimum, the allowable size for implantable devices and the complexity of the communications techniques. The expense of the implanted unit and the programmer thus limits both the number of persons who can obtain the units and the number of hospitals, clinics and doctors which can program the units. Therefore it is undesirable to simply port over pacemaker technology for use in epileptic and other nervous system disorder patients.

SUMMARY OF THE INVENTION

The present invention relates to a more cost effective, implantable stimulator particularly tailored for use in stimulating the vagus nerve to reduce epileptic seizures. A conventional microprocessor is used in conjunction with other standardly available components to form the stimulator. No custom integrated circuitry is utilized. The communications technique is less complicated because it is based on asynchronous serial communication, with the presence of a radio frequency signal indicating one state and no signal indicating the other state. Various passwords, handshakes and parity checks are used to improve data integrity.

The communications circuitry is simplified to reduce the space utilized. The coil and voltage converter used to produce the current supplied to the patient is also used to produce the transmitted signal. The received signal from the programmer can be received by an optimized receiver coil or can be received by the transmitter coil to further save space. To allow the receiver to function without requiring circuitry to cancel or filter any signals produced by the system while supplying current to the patient, which produces a very high interference level environment, the current drive is periodically removed to allow the receiver a clean interval for reception of signals from the programmer. To further improve the radio frequency interface the programmer uses an X-shaped coil pair to allow better coupling between the implanted unit and the programmer.

To further reduce energy consumption the microprocessor controls its own operating voltage and that of other devices so that the microprocessor and the devices use less power during certain intervals and the microprocessor and the devices are activated during more critical operations.

Resetting the system is accomplished by applying both a magnetic field to a reed switch and a radio frequency signal to the receiver circuitry for a given period. This reduces the likelihood of accidental resetting of the unit and thus loss of programmed intervals.

BRIEF DESCRIPTION OF THE DRAWINGS

A better understanding of the present invention can be obtained when the following detailed description of the preferred embodiment is considered in conjunction with the following drawings, in which:

FIGS. 10, 11A and 11B are flowchart illustrations of operating sequences of the programming system of FIG. 2.

DETAILED DESCRIPTION OF THE PREFERRED EMBODIMENT

Figure 1:
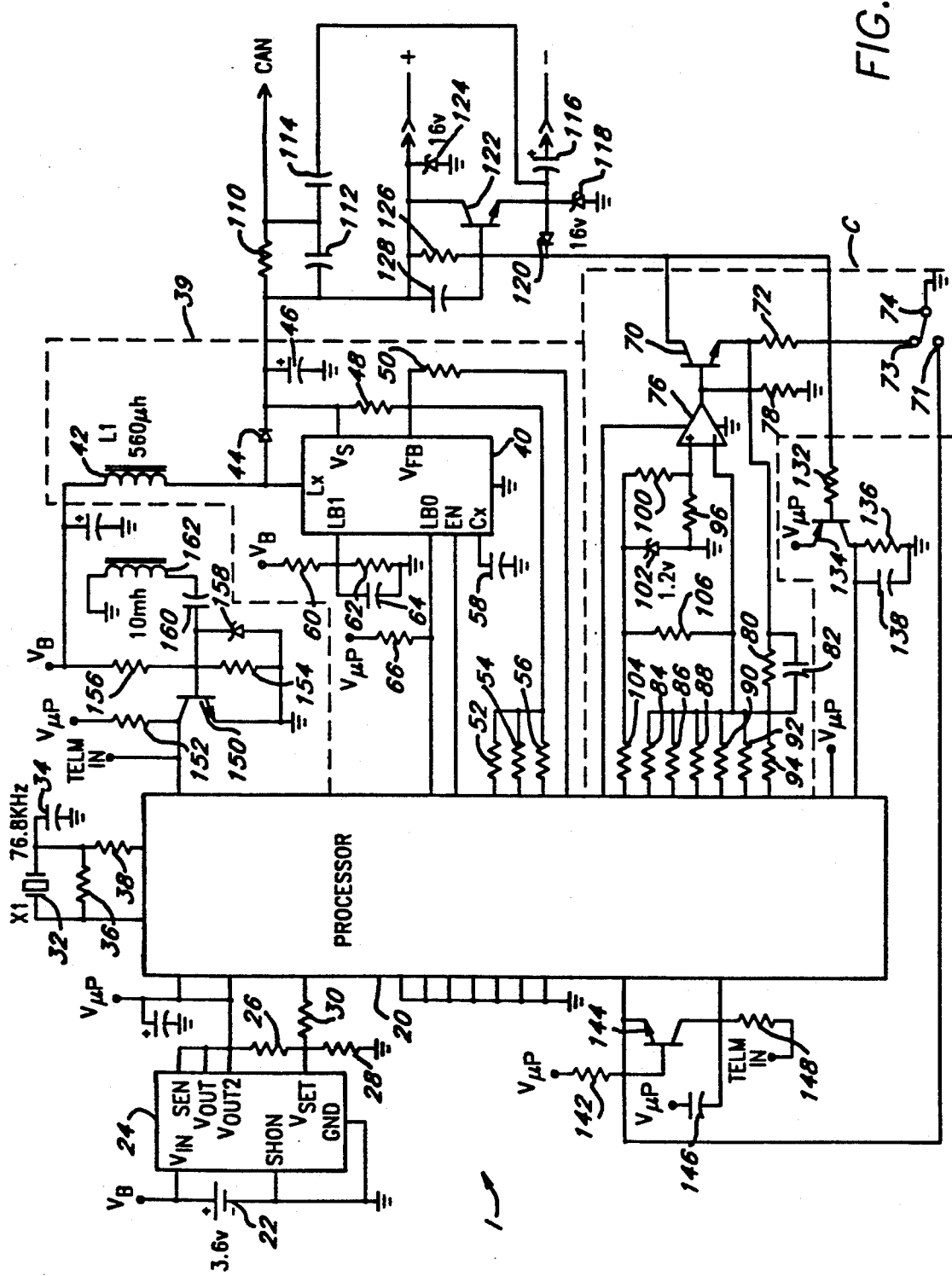
FIG. 1 is a schematic diagram of an implantable stimulator according to the present invention.
Figure 2:
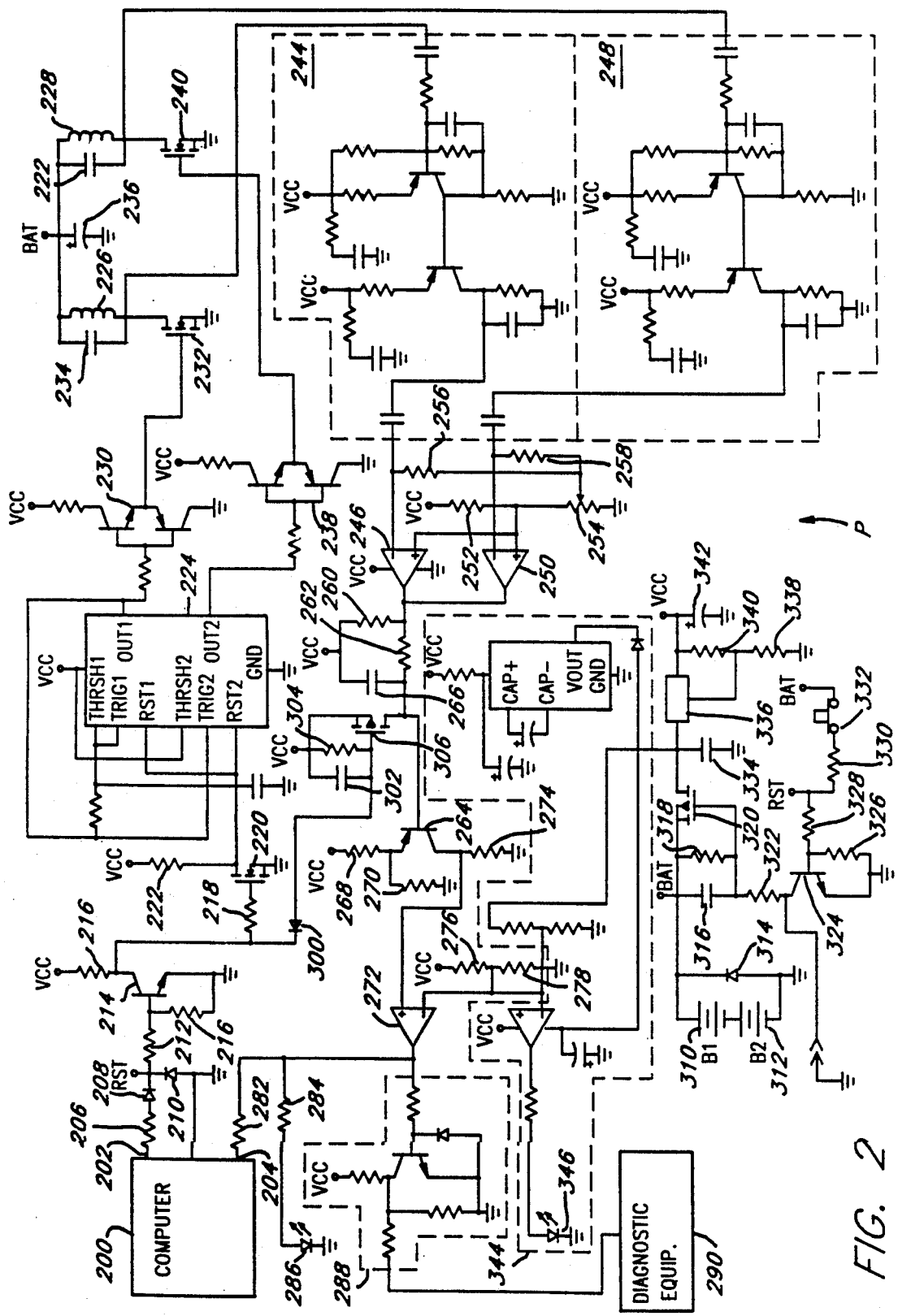
FIG. 2 is a schematic and block diagram of a programming system for use with the implantable stimulator of FIG. 1.

Referring now to FIG. 1 the letter I generally represents electronic componentry installed in the implantable portion of a stimulator according to the present invention. The external portion or programming system (FIG. 2) is generally referred to as the letter P and is used to communicate with the implant I.

The main component of the implant I is a processor 20, preferably a CMOS microcomputer such as the 68C05 available from Motorola Semiconductor Products, Inc. The CMOS version is preferable because this reduces the power consumed by the implant I. The processor 20 includes a series of parallel input and output lines, an asynchronuous serial port and a timer which can generate interrupts. A battery 22 having a battery voltage $V_B$, preferably 3.6 volts, is connected to a programmable positive voltage regulator 24. Regulated voltage outputs from the regulator 24 provide the microprocessor 20 and other components in the system with a voltage referred, to as the microprocessor voltage $V_{up}$. A resistor 26 is connected between the voltage output of the regulator 24 and the voltage set input, with a resistor 28 connected between the voltage set input and ground. This is the basic feedback circuit utilized by the regulator 24 to regulate its output voltage. A control resistor 30 is connected between the voltage set input of the regulator 24 and a digital output of the processor 20 to allow the processor 20 to control its own supply voltage $V_{up}$. In this manner the supply voltage $V_{up}$ can be reduced from 2.8 volts to 1.4 volts during certain operating portions as will be explained to slow down operation of the processor 20 and thereby reduce power consumption. The voltage $V_{up}$ is increased during other operations of the processor 20 when higher speed operation is appropriate. A crystal 32, capacitor 34 and resistors 36 and 38 are connected to the processor 20 according to instructions from the manufacture to produce the clocking signal for the processor 20. In the preferred embodiment the operating frequency is 76.8 kHz, but other values can be utilized if desired.

An up converter 39 based on a CMOS step up switching regulator 40, such as an MAX630 manufactured by Maxim Integrated Product, is used to develop the voltages necessary to drive the electrodes (not shown) connected to the vagus nerve according to U.S. Pat. No. 4,702,254 and to drive the transmitter portions of the implant I. The switching regulator 40 is connected to the battery voltage $V_B$ by means of a transmit/converter coil 42. This transmit/converter coil 42 serves the dual purpose of performing the inductance function in the up converter 39 and serving as the transmitter antenna for the radio frequency transmission portions of the implant I. The transmit/converter coil 42 is connected between the battery voltage $V_B$ and the inductance input of the regulator 40. The anode of a diode 44 is connected to the inductance input of the regulator 40, while the cathode of the diode 44 is connected to the supply voltage input of the regulator 40 and to one side of a capacitor 46. The other side of the capacitor 46 is connected to ground. A resistor 48 is connected between the supply voltage input of the regulator 40 and the feedback or voltage sense input. A resistor 50 has one terminal connected to the feedback voltage input of the regulator 40 and has its other terminal connected to the serial output of the processor 20. The resistor 50 is used to set the feedback voltage to the regulator 40 at either high or low levels as necessary to cause the regulator 40 to produce a large signal during a low phase so that a large RF field is emitted from the coil 42 and no signal during a high phase so no RF field is emitted from the coil 42. This emitted RF field is then the transmitted signal from the implant I during communication or marker phases.

Additionally, three resistors 52, 54 and 56 have one terminal connected to the voltage feedback input of the regulator 40 and their other terminals coupled to three outputs of the processor 20. These three resistors 52, 54 and 56 form a resistor divider network used to program the output voltage of the regulator 40. The regulator 40 is designed such that the inductance output is pulsed whenever the voltage at the feedback terminal is less than 1.31 volts. By varying the voltage applied by the processor 20 to the resistors 52, 54 and 56, as well as resistor 50, the effective resistance to ground from the feedback voltage input can be varied, changing the feedback ratio and thus the output voltage A capacitor 58 used to set the oscillator frequency of the regulator 40 is connected between ground and the capacitor input on the regulator 40. In the preferred embodiment the oscillation frequency is 40 kHz. Two resistors 60 and 62 are connected in series between the battery voltage $V_B$ and ground to form a voltage divider pair. A capacitor 64 is connected in parallel with the resistor 62, which is connected to ground. The connection point between the two resistors 60 and 62 is connected to a battery level sense input of the regulator 40, which provides a low signal on a low battery output if the voltage at the low battery input is below 1.31 volts. The low battery output signal is provided to an input of the processor 20, this signal being pulled up to the microprocessor voltage $V_{up}$ by a resistor 66. Thus in this manner the processor 20 can determine when the battery voltage is low and set an appropriate flag for communication to the programmer P. An output from the processor 20 is connected to an enable input of the regulator 40, to allow the processor 20 to disable operation of the regulator 40 when desired to reduce power consumption of the circuitry in the implant I. The up converter 39 can be powered down when no radio frequency transmissions are occurring and when no drive is being supplied to the electrode.

A programmable current source C provides the constant current which is supplied to the electrodes coupled to the vagus nerve. The current is provided by an NPN transistor 70, whose emitter is connected to a resistor 72 whose other terminal is connected to a normally closed terminal 73 of a reed switch 74. The contact of the reed switch 74 is connected to ground. The reed switch 74 is used for manually initiating a treatment cycle, for disabling the drive to the electrodes and resetting the processor 20. The base of the transistor 70 is connected to the output of an operational amplifier 76 and to one terminal of a resistor 78 whose other terminal is connected to ground. The emitter of the transistor 70 is also connected to the parallel combination of a resistor 80 and a capacitor 82, which form the feedback components for the current source C. The second terminals of the capacitor 82 and the resistor 80 are connected to the inverting input of the amplifier 76. Also connected to the inverting input of the amplifier 76 are six resistors 84, 86, 88, 90, 92 and 94 which effectively form a binary ladder between six outputs of the microprocessor 20 and the inverting input of the amplifier 76. Thus the six resistors 84–94 perform the digital to analog conversion used in making the current source C programmable.

The non-inverting input of the amplifier 76 is connected to one terminal of a resistor 96 whose other terminal is connected to ground. Preferably the resistor 96 is a selected value to allow precise trimming of the accuracy of the current source C. Also connected to the non-inverting input of the amplifier 76 is a resistor 100 whose other terminal is connected to the cathode of a precision voltage reference drawn for illustration purposes as a Zener diode 102 whose anode is connected to ground. Also connected to the cathode of the Zener diode 102 is a resistor 104 which has its other terminal connected to an output of the processor 20. In this way the processor 20 can define a reference drive voltage to be used by the current source amplifier 76. A zero level voltage applied to the resistor 104 shuts off the current source C. A resistor 106 is connected between the cathode of the Zener diode 102 and the inverting input of the amplifier 76 to allow the lowest desired current setting, 0.25 mA, in the preferred embodiment, to be developed. A desired output for the current source C is established by setting a non-zero level on the inverting input of the amplifier 76 by driving the output connected to the resistor 104 high and then driving the six digital to analog resistors 84-94 as desired to set the proper level. Power to the amplifier 76 is provided by an output of the processor 20, allowing the amplifier 76 to be completely shut off during low power consumption periods.

The drive or stepped up voltage as developed at the cathode of the diode 44, the output of the up converter 39, is provided to a resistor 110 whose other terminal is connected to the implant container. In parallel with the resistor 110 is a capacitor 112. A capacitor 114 is connected between the container and a capacitor 116, whose other terminal is connected to the negative electrode. Also connected to capacitor 114 is the cathode of a Zener diode 118, whose anode is connected to ground to limit the voltage that can be applied on the negative electrode. The anode of a diode 120 is connected to the cathode of the Zener diode 118 and has its anode connected to the collector of the transistor 70. An NPN transistor 122 has its emitter connected to the cathode of the Zener diode 118, its base connected to the cathode of the diode 120 and its collector connected to the positive electrode. A Zener diode 124 has its cathode connected to the positive electrode and its anode connected to ground to provide overvoltage protection. A resistor 126 is connected between the drive voltage and the base of the transistor 122 to bias the transistor 122 for operation. A capacitor 128 is connected in parallel with the resistor 126.

The sufficiency of the voltage present at the collector of the transistor 70, which is used to drive the positive electrode, is fed back to the processor 20 for use in determining the proper output voltage of the regulator 40. This is done by having a resistor 132 connected between the collector of the transistor 70 and the base of a PNP transistor 134. The emitter of the transistor 134 is connected to the microprocessor voltage $V_{up}$, while the collector is connected to an input to the processor 20 and the parallel combination of a resistor 36 and a capacitor 138, whose other terminals are connected to ground. In this way if the voltage being supplied to the base of the transistor 134 should go too low, so that the transistor 134 is activated, the processor 20 can sense this point and raise the voltage output of the up converter 39 by appropriately decreasing the effective resistance supplied by the resistors 52, 54 and 56. This increases the available drive voltage so that the programmable current source C is properly driving the desired currents and is not in saturation or limiting.

A normally open contact 71 of the reed switch 24 is connected to an input of the processor 20 and is pulled up to the microprocessor voltage $V_{up}$ by a resistor 142. Also connected to this input of the processor 20 are the base and emitter of an NPN transistor 144. The collector of the transistor 144 is connected to the low true reset input of the processor 20 and to a capacitor which is connected to the microprocessor voltage $V_{up}$. Voltage is supplied to the collector of the transistor 144 by means of a resistor 148 connected between the collector of the transistor 144 and the collector of a transistor 150. The transistor 150 is the drive transistor connected to the serial input of the processor 20 which is used to receive an incoming radio frequency transmission.

The collector of the transistor 150 is pulled up to the microprocessor voltage $V_{up}$ by a resistor 152. The emitter of the transistor 15 connected to ground. The base of the transistor 150 is connected to two bias resistor 154 and 156, the resistor 154 being connected to ground, and the resistor 156 being connected to the battery voltage $V_B$. Also connected between the base of the transistor 150 and ground is a Zener diode 158, which is used to protect the transistor 150 from any received high level input voltages A capacitor 160 is connected between the base of the transistor 150 and one terminal of a receive coil 162. The other terminal of the receive coil 162 is connected to ground. Thus the receive coil 162 receives a burst of radio frequency energy from the programmer P which is then filtered by the capacitor 160 and provided to the transistor 150 as the received input. While in the embodiment shown two separate inductors 42 and 162 are used for the functions of transmission, voltage development and reception, one single coil can be used to serve all three purposes to further save on space in the implant I. The sensitivity of the receive coil 162 and the biasing of the transistor 150 are such that when the up converter 34 is operating the radio frequency field emitted by the transmitting/converting coil 42 interferes with reception by the transistor 150. However, when the up converter 39 is disabled the receive circuitry works properly to receive the transmissions from the programmer P.

If the transistor 150 is turned on for a sufficient period of time, due to the presence of an received signal, and the reed switch 74 is activated, the capacitor 146 is charged to have a potential of the microprocessor voltage $V_{up}$. When the radio frequency signal is removed and the resistor 148 is connected to the microprocessor voltage $V_{up}$ through the resistor 152, transistor 150 is deactivated, a low level will momentarily appear on the reset input of the processor 20 until the capacitor 146 discharges through the resistors 148 and 152, thus allowing the processor 20 to be reset only by the combination of having the reed switch 74 activated and a sufficiently long burst of radio frequency energy received. If the reed switch 74 is not activated, the reset input is kept at a high level because the transistor 144 does not allow the reset input to go to a low level. If the transistor 150 receives a signal, the voltage difference appears across the resistor 148 and the capacitor 146 remains generally discharged. If the magnet is removed before the radio frequency signal is removed, then the capacitor 146 is discharged through the base to collector diode of the transistor 144, resulting in resetting of the processor 20 if the radio frequency signal had been provided for a sufficient time. Thus the reset procedure is place the magnet to activate the reed switch 74, activate the programmer P to broadcast a stream of radio frequency energy for a sufficient time and stop the broadcast. Alternately, the magnet can be removed after a sufficient period of broadcasting.

The radio frequency signals transmitted by the implant I are received by a programmer P (FIG. 2), which also generates the signals received by the implant I. A programmed computer such as a personal computer 200, which has a serial interface, has its serial output line 202 connected to a resistor 206 whose other terminal is connected to the anode of a diode 208. The cathode of the diode 208 is connected to the cathode of a second diode 210 whose anode is connected to ground to provide reverse voltage protection. Also connected to the cathode of the diode 208 is a resistor 212 whose other terminal is connected to the base of an NPN transistor 214. Connected between the base and emitter of the transistor 214 is a resistor 216, with the emitter being connected to ground. The collector of the transistor 214 is pulled to a high voltage level by a resistor 216 and is connected to a resistor 218 who has its other terminal connected to the gate of a n-channel enhancement MOSFET transistor 220. The transistor 214 thus serves as a level shifter and inverter between the serial output signals and the MOSFET 220. The source of the MOSFET 220 is connected to ground while the drain is connected to a resistor 216 which is connected to the logic high level voltage Thus the voltage appearing at the drain of the MOSFET 220 has the same logic state as the signal developed by the computer 200.

The signal developed at the drain of the MOSFET 220 is connected to the reset inputs of a dual multivibrator 224. The first multivibrator 224a in the dual unit 224 is connected for a stable operation, preferably with a frequency of approximately 100 kHz to provide the basic signal which is coupled to the transceiving coils 226 and 228. The output of the first multivibrator 224a is coupled to a push/pull transistor amplifier 230 whose output is connected to the gate of an n-channel enhancement MOSFET transistor 232 whose source is connected to ground and whose drain is connected to one terminal of the parallel combination of the coil 226 and a capacitor 234. The other terminal of the parallel combination of the coil 226 and a capacitor 234 is connected to the battery voltage as supplied by batteries 310 and 312 which power the programmer P. A capacitor 236 is connected between the battery voltage and ground.

The output of the first multivibrator 224a is connected to the trigger input of the second multivibrator 224b of the multivibrator 224 so that the second multivibrator 224b inverts the output of the first multivibrator 224a. These operations can be performed by the multivibrators located on the ICM7556 manufactured by Intersil, Inc. The output of the second multivibrator 224b is connected to a similar push-pull transistor amplifier 238 whose output is similarly connected to the gate of an n-channel enhancement MOSFET 240. The source of the transistor 240 is connected to ground while the drain is connected to the parallel combination of the coil 228 and a capacitor 242 whose other terminals are connected to the battery voltage. The two coils 226 and 228 are preferably located to form an X or cross so that the signal that they produce is in two different planes to increase likelihood of proper reception by the implant I and receipt by the coils 226 and 228 of any signals produced by the implant I.

The drain of the MOSFET 232 is connected to a capacitively coupled amplifier circuit 244 whose output is connected to the inverting input of a comparator 246. The amplifier circuit 244 filters out the 40 kHz carrier frequency of the signal produced by the implant I so that the transmitted serial data is recovered. Similarly, the drain of the MOSFET 240 is connected to a similar capacitively coupled amplifier circuit 248 whose output is connected to the inverting input of a comparator 250. The non-inverting inputs of the comparators 246 and 250 are connected to the junction between resistor 252 and potentiometer 254 whose other terminals are respectively connected to high level voltage and ground. The wiper arm of the potentiometer 254 is connected to two resistors 256 and 258 which are connected, respectively, to the inverting inputs of the comparators 246 and 250. Thus should either coil 226 or 228 receive a sufficient signal, the signal is amplified by the appropriate amplifier 244 or 248 and applied to the comparator 246 or 250 so that a low level signal develops at the output of the appropriate comparator 246 or 250. The outputs of the two comparators 246 and 250 are connected together and pulled up to a logic high level by a resistor 260. The output of the comparators 246 and 250 is also applied to a resistor 262, whose other terminal is connected to the base of a PNP transistor 264 and to one terminal of a capacitor 266. The second terminal of the capacitor 266 is tied to a high level voltage for noise filtering. The signal which is applied to the base of the transistor 264 is essentially an inverted form of the signal supplied by the serial output of the processor 20, which is applied to the resistor 50 to control the voltage level output of the regulator 40.

The emitter of the transistor 264 is connected to the junction point of two resistors 268 and 270 whose other terminals are connected to, respectively, voltage high level and ground. The collector of the transistor 264 is connected to the non-inverting input of an operational amplifier 272 and to a resistor 274 whose other terminal is connected to ground. The inverting input of the comparator 272 is connected to the junction point between a resistor divider pair formed by resistors 276 and 278, whose other terminals are respectively connected to ground and a high level voltage to set a reference level. The output of the amplifier 272 is provided through a resistor 280 to the serial input of the computer 200 and through a resistor 284 to the anode of a light emitting diode (LED) 286 whose cathode is connected to ground. Thus the amplifier 272 is the driver to produce the proper levels of the serial signal provided to the computer 200. The LED 286 is used to indicate when a signal is being received from the implant I, which signal is supplied to the computer 200. Thus the computer 200 can communicate with the implant I via its conventional serial link.

Additionally, the output of the operational amplifier 272 is provided to a level shifting inverter 288, which provides a signal to diagnostic equipment 290. The diagnostic equipment 290 can thus receive marker pulses which are produced by the implant I under certain conditions. The marker pulses are provided to allow the diagnostic equipment 290 to synchronize with the implant I to allow easier analysis and diagnosis of the implant's operation and the patient's condition.

To prevent the computer 200 from receiving a false signal when it is transmitting, the cathode of a diode 300 is connected to the collector of the transistor 214. The anode of the diode 300 is connected to one terminal of a capacitor 302, one terminal of a resistor 304 and the gate of a P channel enhancement MOSFET 306. The second terminals of the capacitor 302 and resistor 304 are connected to a high voltage level, as is the source of the MOSFET 306. The drain of the MOSFET 306 is connected to the base of the transistor 264, so that whenever the multivibrator 224 is activated, causing a radio frequency signal to be transmitted to the implant I, the transistor 264 is clamped to a high level voltage so that no signal is provided to the amplifier 272 and thus back to the computer 200.

Power is supplied to the programmer P by two batteries 310 and 312, which are connected in series with each other and in parallel with a diode 314. The diode is connected with the cathode connected to the positive voltage and the anode connected to ground. The positive battery voltage BAT is applied to a capacitor 316, a resistor 318 and the source of a P channel enhancement MOSFET 320. The gate of the MOSFET 320 and the second terminals of the capacitor 316 and the resistor 318 are connected to one terminal of a resistor 322, whose other terminal is connected to ground and to the collector of an NPN transistor 324. The connection to ground is used only when the programmer P is connected to the computer 200, thereby enabling the MOSFET 320 to provide voltage to a voltage regulator 336 which provides the power for the remaining components in the programmer P when the programmer P is connected to the computer 200. The emitter of the transistor 324 is connected to ground, while the base is connected to a resistor 326, whose other terminal is connected to ground, and to a resistor 328. The second terminal of the resistor 328 is connected to one terminal of a resistor 330, whose other terminal is connected to one terminal of a reset switch 332. The other terminal of the reset switch 332 is connected to the battery voltage BAT. The signal present at the junction of the resistors 328 and 330 is provided to the cathode of the diode 208. In this way if the ground is removed from the collector of transistor 324 because the computer 200 is not connected, the reset switch 332 can then be used to provide a signal to the transistor 324, activating the series MOSFET 320 and simultaneously activating the multivibrator 224 to begin a continuous transmission. If the reset switch 332 is held for a sufficient period, 20-25 seconds in the preferred embodiment, the implant I resets, assuming the magnet is in location as described above. Thus the implant I can be reset when the programmer P is not available.

The drain of the series MOSFET 320 is connected to a capacitor 334 connected to ground and to the input terminal of a three terminal voltage regulator 336. The reference leg of the three terminal regulator 336 is tied between two resistors 338 and 340, with the resistor 338 being connected to ground and the resistor 340 being connected to the output of the regulator 336. The output of the regulator 336 is the high logic level voltage used in the programmer P and has a capacitor 342 connected to ground for filtering purposes. The input voltage to the three terminal regulator 336 is also provided to a low battery indication circuit 344 which has an LED 346 to provide a low battery indication.

Thus the programmer P can be used with the computer 200 to provide commands to or receive messages from the implant I or can be used uncoupled from the computer 200 to reset the implant I when used in conjunction with the magnet used to control the reed switch 74.

Figure 3A:
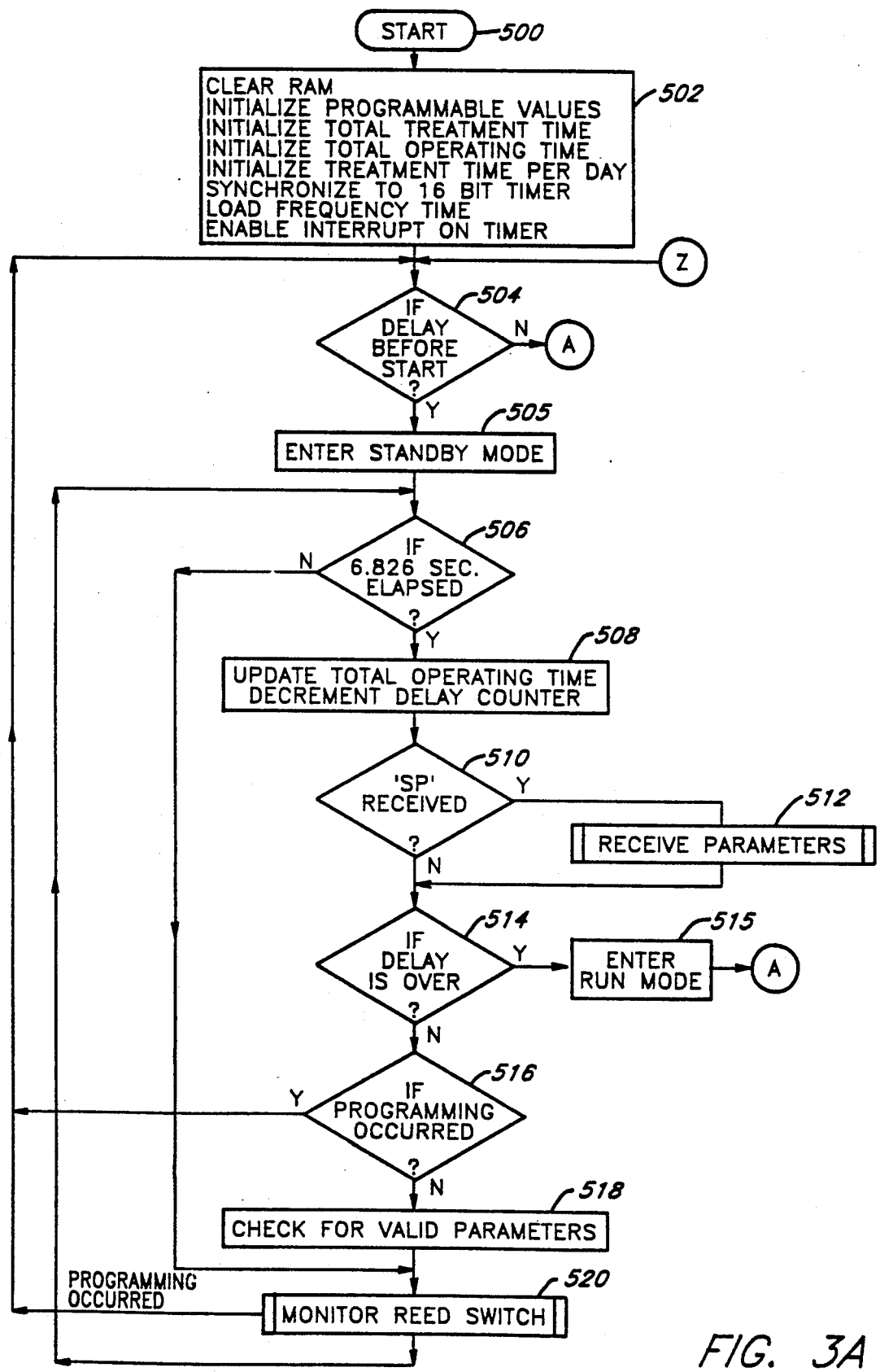
FIGS. 3A, 3B, 3C, 3D, 4, 5A and 5B are flowchart illustrations of operating sequences of the implant of FIG. 1.

The operating sequence of the implant I commences at the start sequence 500 (FIG. 3A). In the first step of the start sequence 500, step 502, the processor 20 clears the memory; initializes all programmable values, such as the parameters utilized with the serial port contained in the processor 20; initializes the total treatment time to zero hours; initializes the total operating time at 1 hour; initializes the treatment time per day at 24 hours; initializes default normal and magnet mode stimulation pulse amplitudes and frequencies; sets the stimulation interval at 60 minutes and sets a zero hour delay. In step 502 the processor 20 also increases the voltage supplied by the regulator 24 and programs the up converter 39 and the current source C. Finally in step 502 the processor 20 sets up the internal timer and enables its interrupt. The timer is preferably set to overflow every 6.826 seconds.

Figure 3B:
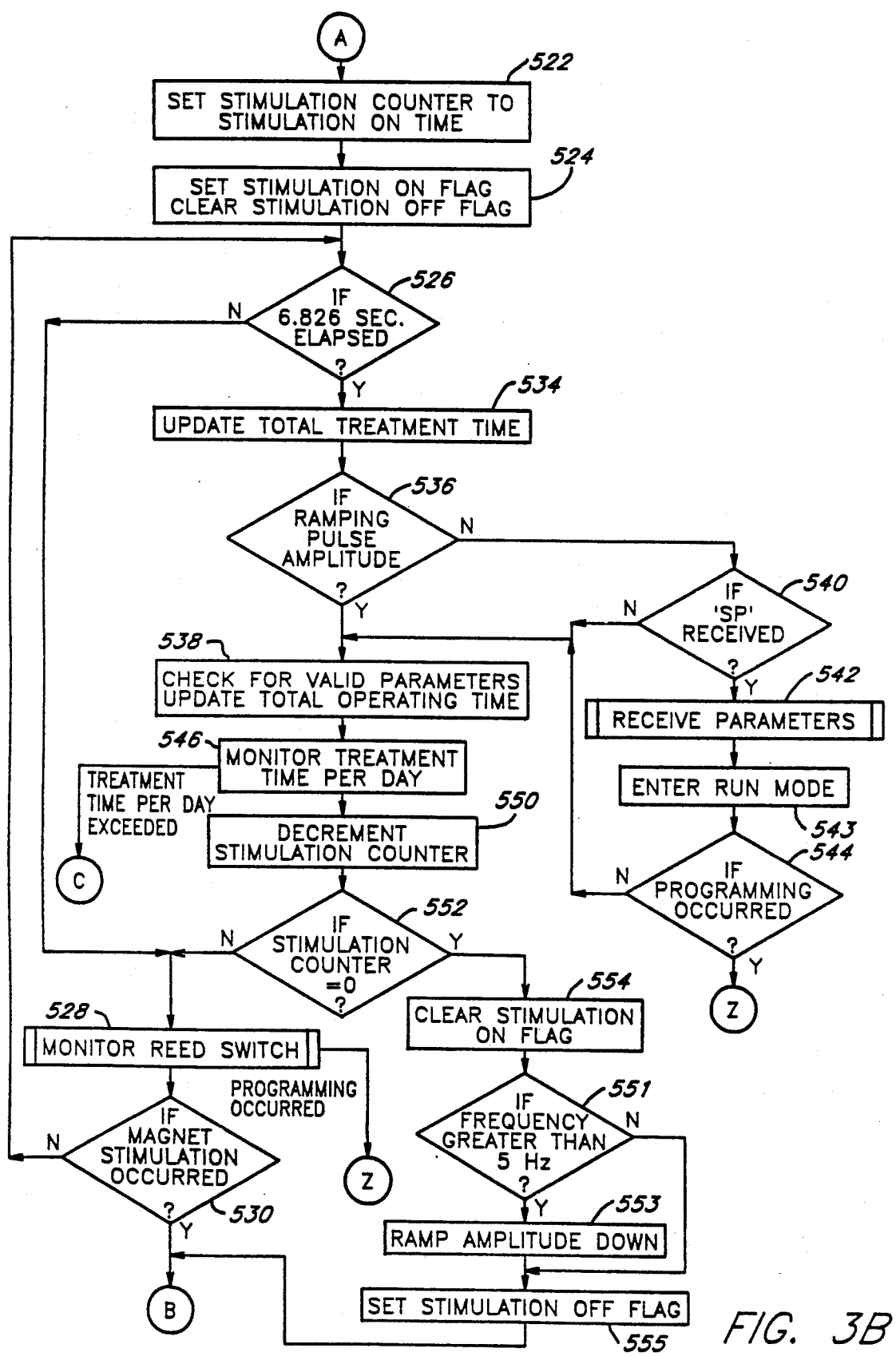
Figure 4:
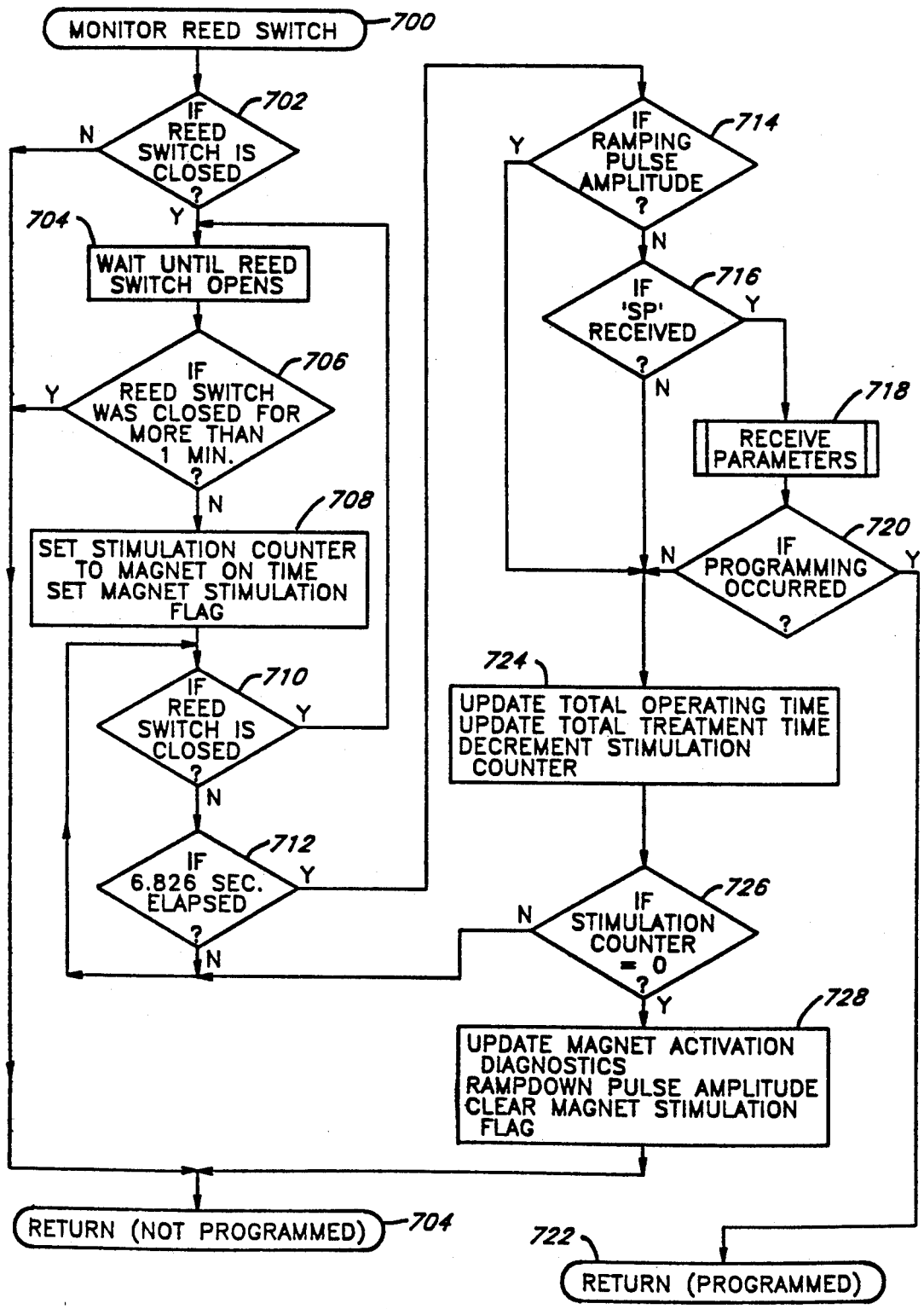

Control then proceeds to step 504 to determine if a delay is necessary before treatment is to be started. If there was no delay before starting operation in step 504 control proceeds to step 522 (FIG. 3B). If there is a delay, control proceeds to step 505 where the implant I is placed in standby mode. In standby mode the up converter 39 is disabled, power is removed from the amplifier 72 and the microprocessor voltage $V_{up}$ is set to the low level. Control then proceeds to step 506 where a determination is made if 6.826 seconds has elapsed by checking the timer overflow bit. This 6.826 second period is the interval between samplings of the serial port to determine if the programmer P is attempting to communicate with the implant I. If the time period has elapsed, control proceeds to step 508 where the total operating time is updated to indicate the passage of the 6.826 second interval and the delay counter is decremented. Control then proceeds to step 510 to determine if a space character with proper parity has been received over the communication interface during a 300 msec window. This is done by shutting off the up converter 39 for approximately 300 msec and monitoring the serial port. Thus the noise generated by the up converter 39 is removed periodically, allowing the receive circuitry to be greatly simplified. If a space character with proper parity has been received, this is an indication that the programmer P is attempting to communicate with the implant I and therefore control proceeds to step 512, the receive parameters sequence. After the parameters have been received in step 512 or if a space was not received during the listening interval, control proceeds to step 514 to check to see if the delay period is over. If not, control proceeds to step 516 to determine if programming occurred in step 512. If so, control returns to step 504 to reinitiate the loop. If no programming occurred, control proceeds to step 518 where the various parameters, such as pulse amplitude, pulse frequency, pulse width, magnet activation pulse width, stimulation burst time, simulation burst interval, treatment time of day, magnet activation amplitude, and magnet activation stimulation burst time, are checked to see if the parameters are valid. If not, valid parameters are loaded. Control then proceeds to step 520 where the monitor reed switch sequence 700 (FIG. 4) is called to determine if manual activation is desired. There are two exits from the monitor reed switch routine 700, with the first occurring if programming occurred, in which case control proceeds to step 504. If programming of the parameters did not occur during the monitor reed switch routine 700, control proceeds from step 520 to step 506.

Figure 3C:
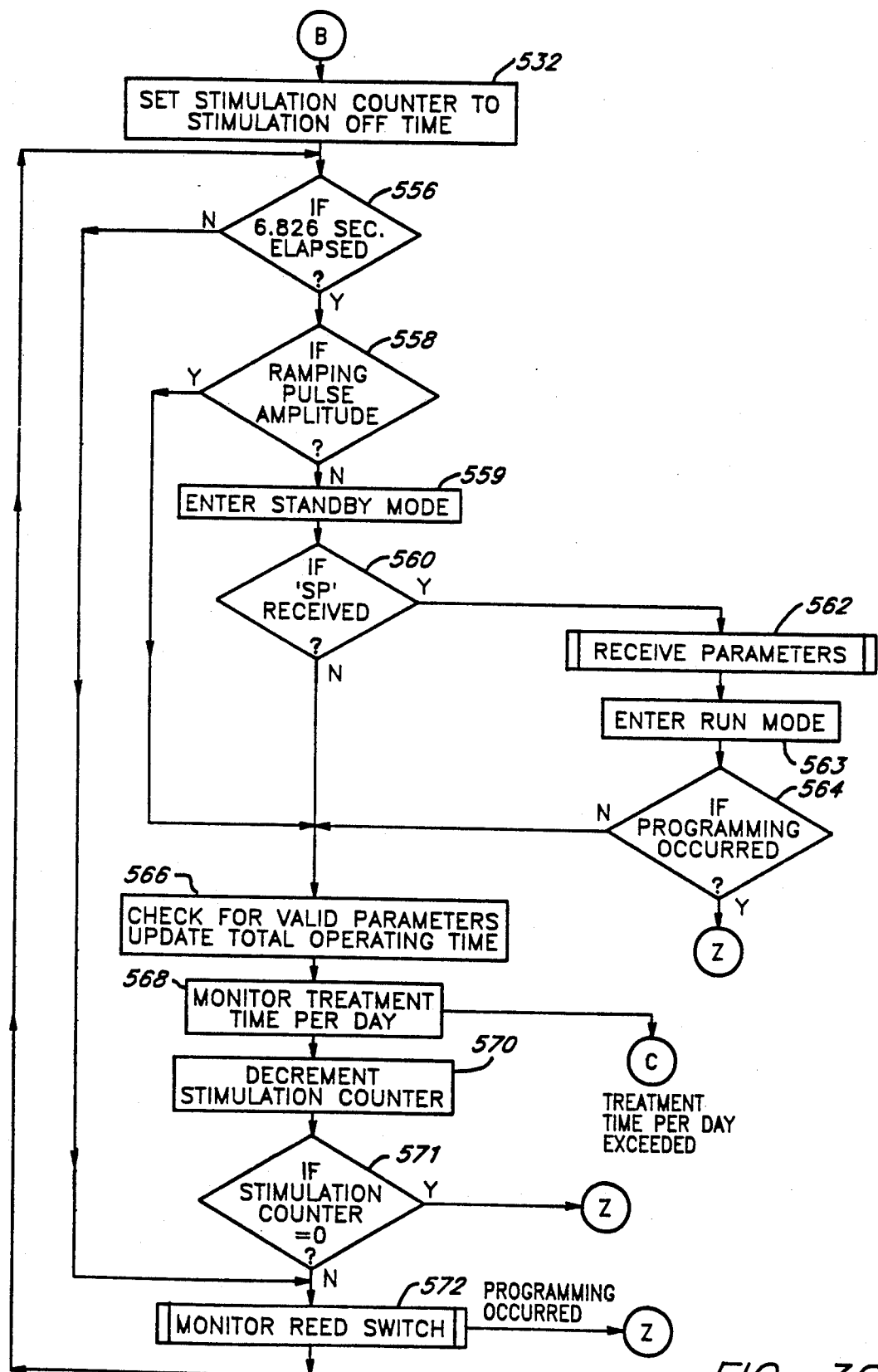

If the delay time was over in step 514, control proceeds to step 515, where the implant I is placed in run mode. The microprocessor voltage $V_{up}$ is increased to the high level, the up convertor 39 is enabled and power is supplied to the amplifier 74. Control then proceeds to step 522 where an internal value referred to as the stimulation counter is set to stimulation on time. In step 524 a flag is set indicating that stimulation is on and a stimulation off flag is cleared. Control proceeds to step 526 to determine if 6.826 seconds have elapsed and it is time to monitor for a communications attempt If not, control proceeds to step 528 which is a reference to the monitor reed switch sequence 700. If programming occurs during this operation of the monitor reed switch sequence 700, control proceeds from step 528 to step 504. If no programming occurred, control proceeds to step 530 to determine if magnet stimulation occurred. If not, control proceeds to step 526. If magnet stimulation did occur, control proceeds to step 532 (FIG. 3C).

If the 6.826 second period has elapsed in step 526, control proceeds to step 534 to update the total treatment time and then to step 536 to see if the implant I is in the process of ramping the pulse amplitude. If so, control proceeds to step 538. If ramping is not in effect, control proceeds from step 536 to step 540 to determine if a space character has been received using the process described in step 510. If not, control proceeds to step 538. If a space has been received control proceeds to the receive parameter sequence in step 542. After completing the receive parameter sequence 600, step 542 transfers control to step 543 where the implant I is placed in run mode. Control then proceeds to step 544 to determine if programming occurred during the receive parameter sequence. If so, control returns to step 504. If not, control proceeds to step 538.

Figure 3D:
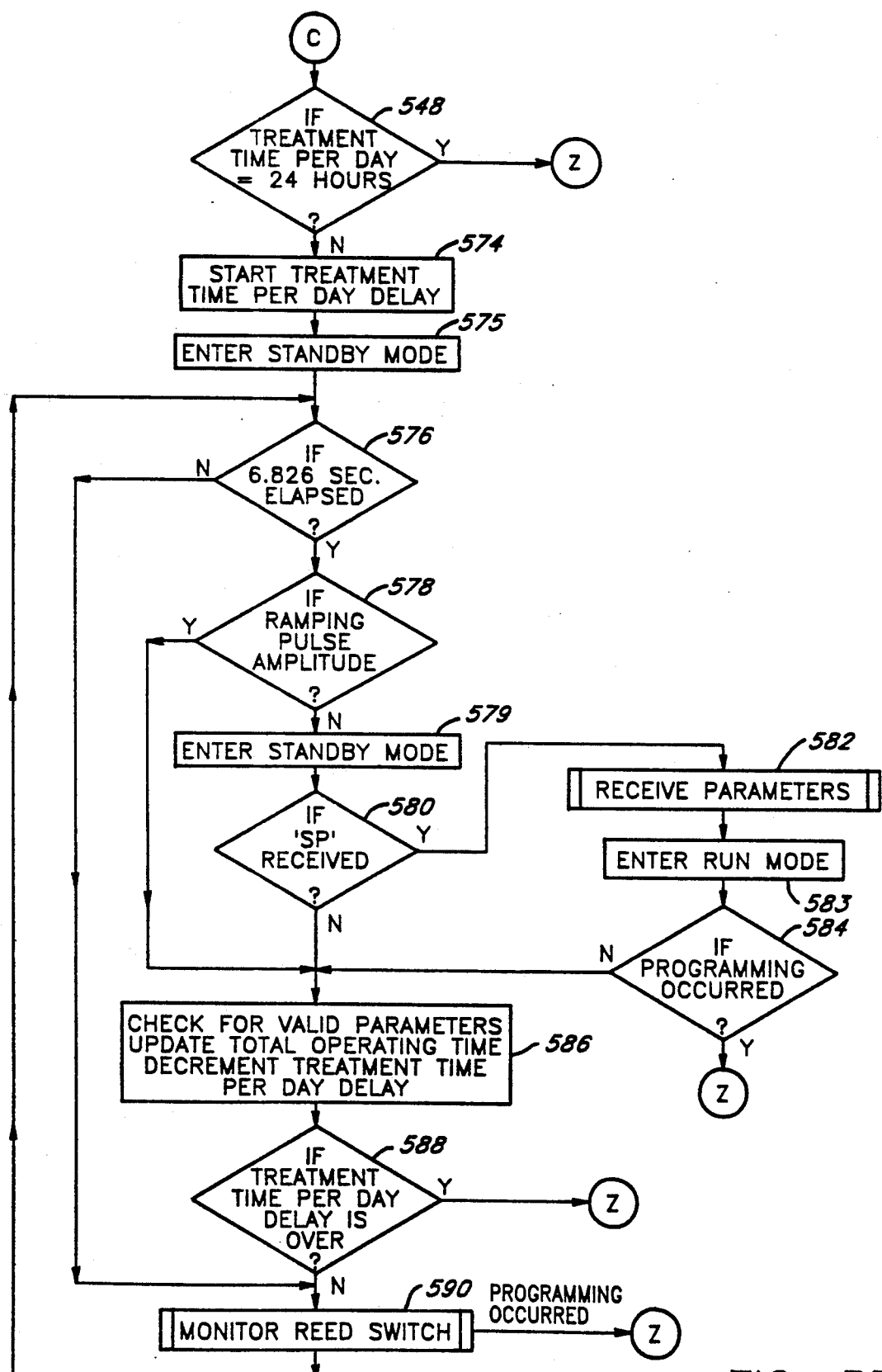

In step 538 the processor 20 determines whether the parameters as indicated above are valid and updates the total operating time to indicate the 6.826 second elapsed time. Control proceeds to step 546 where the total treatment time for the day is monitored. If the total treatment time for the day has been exceeded, then control proceeds to step 548 (FIG. 3D). If the treatment time has not been exceeded, control proceeds to step 550 which decrements the stimulation counter to reduce the remaining stimulation time. Control then proceeds to step 552 to determine if the stimulation counter is zero. If the counter is not zero, indicating that the stimulation period has not ended, control proceeds to step 528. If the stimulation counter is equal to zero, this indicates an end to the stimulation period and control proceeds to step 554. In step 554 the stimulation on flag is cleared. Control proceeds to step 551 where the processor 20 determines if the stimulation pulse frequency is greater than 5 Hz. If so, control proceeds to step 553 to cause the pulse to ramp down. Control proceeds to step 555, which is also where control proceeds if the stimulator pulse frequency is not greater than 5 Hz. In step 555 the stimulation off flag is set. Control then proceeds to step 532.

In step 532 the stimulation counter value is set to that of the stimulation off time and control proceeds to step 556. In step 556 a determination is made as to whether a 6.826 second period has elapsed. If so, control proceeds to step 558 to determine if the pulse amplitude is ramping down. If not, control proceeds to step 559 where standby mode is entered. Control proceeds to step 560 to determine if a space character is received over the communication interface during the listening period. If so, control proceeds to step 562, which calls the receive parameter sequence to proceed with the communication sequence. After completing the communication sequence, control proceeds from step 562 to step 563 where run mode is activated. Control proceeds to step 564 where a determination is made as to whether programming did occur in the receive parameter sequence. If so, control proceeds to step 504. If not, control proceeds to step 566 which is also where control proceeds if the space character has not been received in step 560 or if the pulse amplitude was ramping as determined in step 558.

In step 566 the processor 20 checks for valid parameters and updates the total operating time. Control then proceeds to step 568 where the total treatment time per day is monitored and adjusted. If the total treatment time per day has been exceeded, control proceeds to step 548. If the time has not been exceeded, control proceeds to step 570 where the stimulation counter is decremented to count down the off time. In step 571, which follows step 570, the processor 20 determines if the stimulation counter equals zero. If so, control proceeds to step 504. If the off time has not been completed, control proceeds to step 572 which calls the monitor reed switch sequence 700. If programming occurred during the operation of the monitor reed switch sequence 700, control proceeds to step 504. If no programming occurred, control proceeds to step 556 to loop during the off interval. Thus, under general operating conditions the processor 20 will loop between the stimulation off and stimulation on time sequences.

If the treatment time per day has been exceeded in steps 546 or 568, control proceeds to step 548 (FIG. 3D) where a determination is made as to whether the treatment time per day is 24 hours per day. If so, control returns to step 504. If treatment is not enabled all 24 hours of a day control proceeds to step 574, where the treatment time per day delay is loaded into a counter. Control proceeds to step 575 where the processor 20 places the implant I in standby mode. Control proceeds to step 576 to determine if a 6.826 second period has elapsed. If so, control proceeds to step 578 to determine if the pulse amplitude is in a ramp mode. If not, control proceeds to step 579 where the implant I is placed in standby mode. Control proceeds to step 580 to determine if a space character is received during the listening period. If so, control proceeds to step 582 which calls the receive parameter sequence to perform any communications. Control proceeds from step 582 to step 583 where the implant I is placed in run mode. Control proceeds to step 584 to determine if programming had occurred. If so, control returns to step 504. If not, control proceeds to step 586, which is also where control proceeds from step 580 if a space character was not received or from step 578 if the amplitude was ramping.

In step 586 a check is made to determine if the parameters are still valid, the total operating time is updated and the treatment time per day delay is decremented. Control then proceeds to step 588 to determine if the treatment time per day delay is over. If so, control proceeds to step 504 and treatment commences. If not, control proceeds to step 590, which is also where control proceeds if the 6.826 second period has not elapsed in step 576. In step 590 the monitor reed switch sequence 700 is called. If programming occurs during the monitor reed switch sequence 700, control proceeds to step 504. If no programming occurred, control proceeds from step 590 to step 576 to complete the delay period until the next treatment time.

The monitor reed switch sequence 700 commences at step 702, where the processor 20 determines whether the reed switch 74 is closed by the magnet by interrogating the input port. If not, control proceeds to step 704 which is a return from the sequence which indicates that programming was not accomplished. If the reed switch 74 is closed, control proceeds to step 704 where the processor 20 waits until the reed switch 74 is opened, that is, the magnet removed. Control then proceeds to step 706 where the closure time of the reed switch 74 is evaluated to determine if it was closed more than one minute. If so, this is an erroneous condition and control proceeds to step 704. If not, control proceeds to step 708 where a magnet stimulation flag is set and the stimulation counter is set to the magnet stimulation on time. This is the time in which stimulation is provided based on a manual demand. This feature allows the user or treating physician to trigger stimulation at any desired time. The use of programmed and manually triggered stimulation times and pulse parameters permits different treatment modalities if desired.

Control proceeds from step 708 to step 710, where processor 20 determines if the reed switch 74 is closed, after a given interval to allow the reed switch 74 to finish bouncing. If the reed switch 74 is still closed, then control returns to step 704. If the reed switch 74 is not closed after the debounce time, control proceeds to step 712 to determine if 6.826 seconds have elapsed. If not, control returns to step 710. If the time period has elapsed, control proceeds to step 714 to determine if the applied signal is in ramping mode. If not, control proceeds to step 716 to determine if a space character is received during a listening period. If so, control proceeds to step 718 where the receive parameter sequence 600 is called. Control then proceeds to step 720 after returning from the receive parameter sequence 600 called in step 718. In step 720 the processor 20 determines whether programming occurred. If programming had occurred, control proceeds to step 722 which is a return from the monitor reed switch sequence 700 which indicates that programming had occurred. If programming had not occurred in step 720, control proceeds to step 724, which is also where control proceeds from step 716 if a space has not been received or from step 714 if the pulse was in ramping mode.

In step 724 the total operating time is updated by incrementing its value, the total treatment time is updated by incrementing to the proper value and the stimulation counter is decremented to indicate the reduction of the remaining period of stimulation. Control then proceeds to step 726 to determine if the stimulation counter has reached a zero value. If not, control returns to step 710. If the counter value has reached zero, then the manually activated stimulation period has completed and control proceeds to step 728, where the magnet activation diagnostics are updated to indicate an additional magnet activation and the total operating time at which the magnet was activated. These values can be used for various purposes by the physician. Also in step 728 the pulse amplitude is ramped down if necessary and the magnet stimulation flag is cleared to indicate that magnet stimulation is not occurring. Control then proceeds to step 704 for a not programmed return to the calling sequence.

Figure 5A:
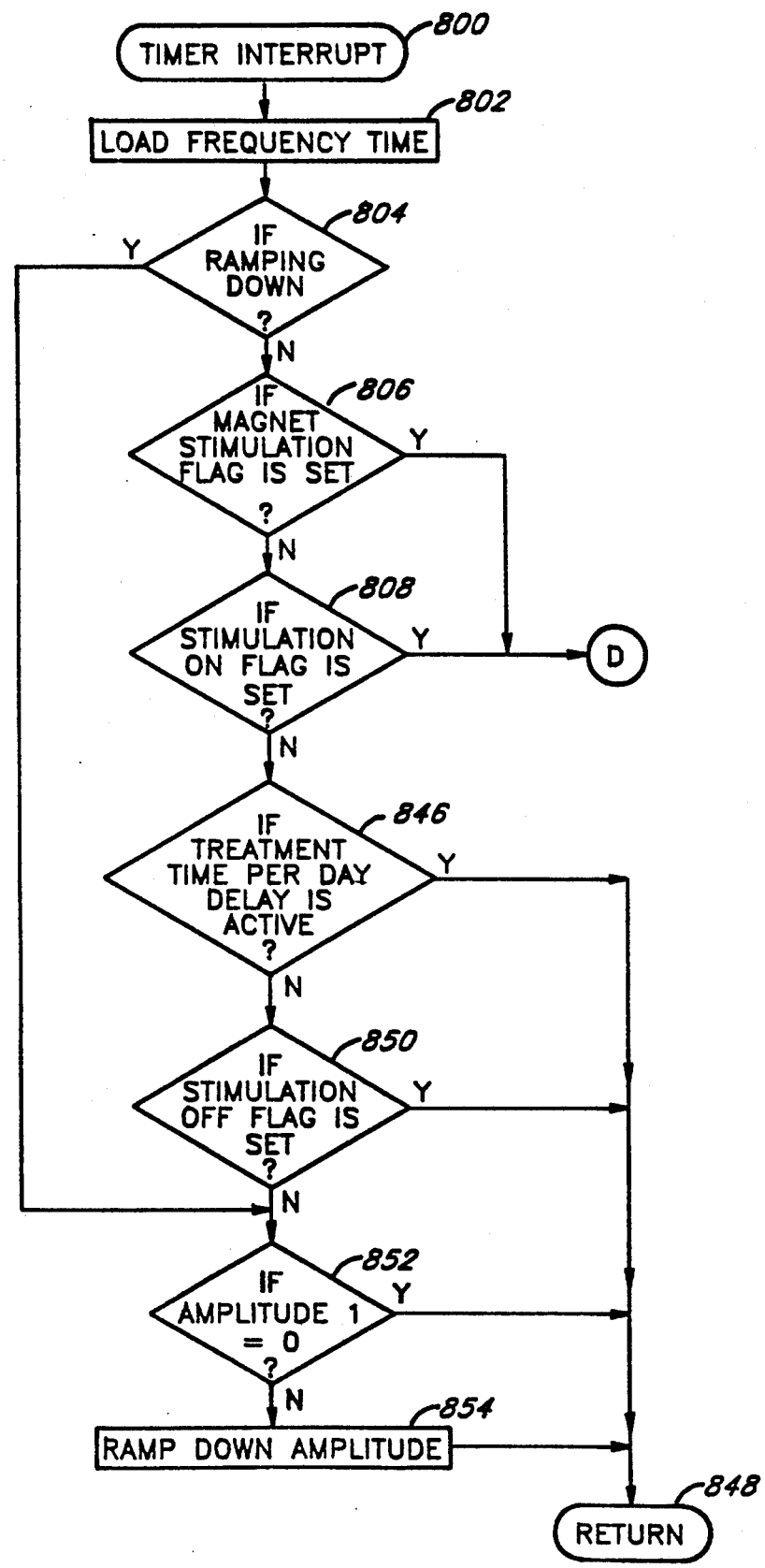
Figure 5B:
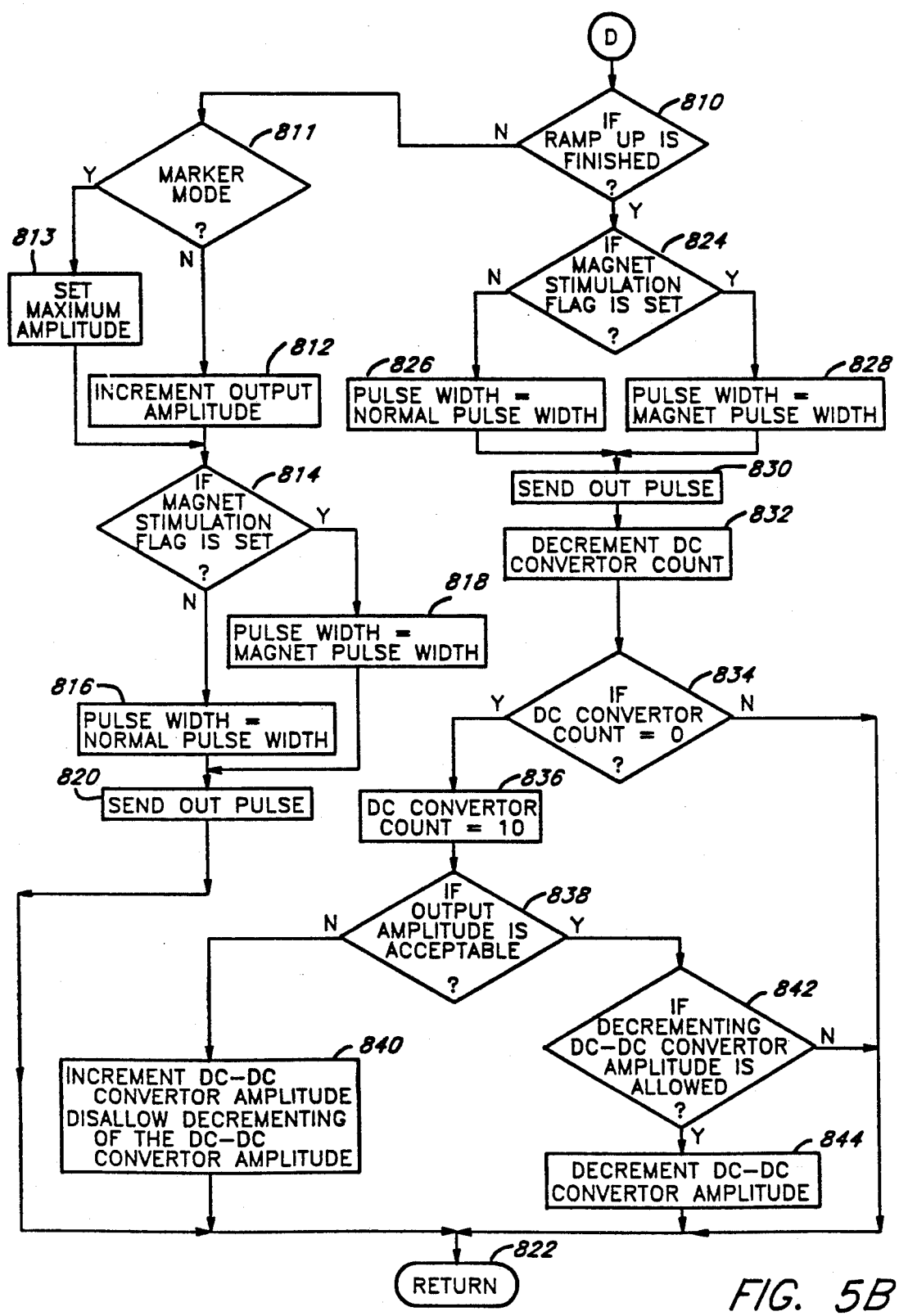

The timer interrupt 800 (FIG. 5A) is an interrupt routine which operates transparent to or in the background of all of the proceeding sequences. The timer interrupt routine operates whenever the internal timer value has counted to equal the value in a compare register which is loaded by the processor 20. During stimulation this value is set so that the interrupts occur at the stimulation frequency. The timer interrupt routine 800 starts at step 802 where the timer is loaded with the frequency value or time to develop the pulse spacing of the applied pulse. In this manner the timer is actually utilized to control the pulse width of the applied treatment pulses. Control proceeds to step 804 to determine if the ramp down process is occurring. If not, control proceeds to step 806 to determine if the magnet stimulation flag is set. If not, control proceeds to step 808 to determine if the stimulation on flag is set. If the answer was yes in either of steps 806 or 808, control proceeds to step 810 (FIG. 5B) to determine if a ramp up is finished. If the ramp up is not finished, control proceeds to step 811 where a determination is made if the stimulation frequency is 5 Hz or less, which indicates the implant I is in marker mode. If so, control proceeds to step 813 where the output current is set to the desired maximum. Control proceeds to step 814. If not in marker mode, control proceeds to step 812 which increases the pulse output current amplitude by one counter value of the D/A convertor as developed by the resistors 84-94. Control then proceeds to step 814 to determine if the magnet stimulation flag is set. If not, control proceeds to step and the pulse width of the particular output is set to be that of the normal pulse width. If the stimulation flag is set as determined in step 814, control proceeds to step 818 where the pulse width is set to the magnet pulse width as set in the parameters. After step 816 or step control proceeds to step 820, where the treatment pulse is transmitted. The pulse is developed by enabling the appropriate resistors 84-94 to ground, not enabling the other resistors 84-94, providing the voltage reference to the amplifier 74 and activating the up converter 39. The pulse time is developed in a software timing loop. Control proceeds to step 822, which is a return from the timer interrupt routine 800 to the interrupted instruction.

If at step 810 it is determined that a ramp up is finished, control proceeds to step 824 to determine if the magnet stimulation flag is set. If not, control proceeds to step 826 where the pulse width is set to be the normal pulse width. If the magnet stimulation flag is set in step 824, control proceeds to step 828 where the pulse width for the pulse to be developed is set to the magnet pulse width value. Control proceeds from either step 826 or step 828 to step 830, where the treatment pulse is transmitted. Control proceeds to step 832 where a counter used to determine if it is time to try and reduce the value being applied to the up convertor 39 is decremented. It is desirable to set the up convertor voltage at the lowest possible voltage and yet have sufficient margin to insure the desired current is actually being supplied to the patient.

Control proceeds to step 834 to determine if the up convertor count value is equal to zero. If the up convertor count is not equal to zero, this is an indication that it is not appropriate at this point to check the output amplitude value. Control then proceeds to step 822 for a return to the interrupted sequence. If the up convertor count is equal to zero, then control proceeds to step 836 where the count value is reinitiated to ten, so that every ten cycles through the timer interrupt routine 800 the voltage value may be evaluated. Control then proceeds to step 838, where the voltage level of the collector of the transistor 134 is evaluated to determine if the output voltage amplitude is acceptable. If the amplitude is not acceptable, control proceeds from step 838 to step 840 where the up convertor output amplitude is incremented to provide more voltage and a flag is set indicating that the up convertor output value should not be decremented. Control then proceeds to step 822 for a return from the timer interrupt routine 800.

If the output amplitude is acceptable in step 838, control proceeds to step 842 where the processor 20 determines if the up convertor amplitude can be decremented. If not, control proceeds to step 822. If the up convertor amplitude can be decremented, control proceeds to step 844 where the up convertor amplitude is actually decremented. In this manner the voltage supplied by the up convertor 39 is reduced if desirable to conserve energy and to limit the applied voltage. Control proceeds to step 822.

If in step 808 it is determined that the stimulation on flag is not set, control proceeds to step 846 to determine if the treatment time per day delay is active, that is, if stimulation should not occur for a given period. If so, control proceeds to step 848, which is a return to the interrupted sequence. If the treatment time per day delay is not active, control proceeds from step 846 to step 850 to determine if the stimulation off flag is set. If so, control proceeds to step 848. If not, control proceeds to step 852, which is also where control would proceed if it was determined in step 804 that the implant I was ramping down the applied signal. In step 852 the processor 20 determines whether the amplitude of the applied pulse is equal to zero. If it is, control proceeds to step 848. If it is not equal to zero, control proceeds to step 854 where the amplitude of the applied signal is decremented. Control then proceeds to step 848 for a return from the time interrupt routine 800.

Therefore the implant I is operating at full power only during stimulation times and at other periods is operating at reduced power levels to conserve battery life. At all times, even during stimulation intervals, the implant I periodically reduces its radio frequency emissions and monitors a communication channel, increasing the reliability of the receiver circuitry. When the implant I is providing stimulation at below a given frequency marker pulses are developed to allow diagnostic equipment to monitor implant I operation. Additionally, by using parity and multiple handshaking of data being transmitted from the programmer P to the implant I data errors are reduced and simple communications circuitry can be used.

The foregoing disclosure and description of the invention are illustrative and explanatory thereof, and various changes in the size, shape, materials, components, circuitry, wiring connections and contacts, as well as in the details of the illustrated circuitry, construction and contacts, as well as in the details of the illustrated circuitry, construction and method of operation may be made without departing from the spirit of the invention.

What is claimed is:

1. A microprocessor reset circuit, comprising:
   a microprocessor having a reset input;
   means for receiving a radio frequency transmission and producing an output signal;
   means for sensing the presence of a magnetic field; and
   means connected to said radio frequency transmission means, to said magnetic field sensing means and to said microprocessor reset input for providing a signal to said microprocessor reset input if said magnetic field is present while a radio frequency transmission is received for at least a predetermined interval.

2. The circuit of claim 1, wherein said magnetic field sensing means includes a reed switch.

3. The circuit of claim 2, further comprising:
   a voltage source providing a ground reference and a high voltage level for developing logic high and logic low voltage levels, said voltage source connected to said microprocessor, said radio frequency transmission receiving means, said magnetic field sensing means and said reset signal means, and
   wherein said radio frequency transmission receiving means includes a transistor having an output and connected to provide a logic low voltage on said output as said output signal when said radio frequency transmission is present.

4. The circuit of claim 3, wherein said reset signal means includes a capacitor connected to said reset input and to a logic high voltage level.

5. The circuit of claim 4, further comprising:
   a resistor connected between said microprocessor reset input and said transistor output, and
   wherein said resistor output is connected to provide a logic high voltage on said output when said radio frequency transmission is not present and wherein said microprocessor resets when a logic low level is present at said reset input.

6. The circuit of claim 5, wherein said reed switch has a first terminal connected to ground to provide a logic low level and a second terminal connected to said first terminal when a magnetic field is present and open when no magnetic field is present.
   the circuit further comprising a resistor connected to said voltage source high voltage level and said reed switch second terminal to produce a logic high level on said reed switch second terminal when a magnetic field is not present and a logic low level when a magnetic field is present; and a device connected between said reed switch second terminal and said reset input which allows current to flow from said reed switch second terminal to said reset input when the voltage of said reed switch second terminal is an amount greater than said reset input.

* * * * *